United States Patent

Stoltefuss et al.

Patent Number: 5,502,062
Date of Patent: Mar. 26, 1996

[54] 2-AMINO-4-QUINOLYL-DIHYDROPYRIDINES, PROCESSES FOR THEIR PREPARATION, AND THEIR USE

[75] Inventors: Jürgen Stoltefuss, Haan; Siegfried Goldmann, Wuppertal; Alexander Straub, Wuppertal; Martin Bechem, Wuppertal; Rainer Gross, Wuppertal; Siegbert Hebisch, Bottrop; Joachim Hütter; Howard-Paul Rounding, both of Wuppertal, all of Germany

[73] Assignee: Bayer Aktiengesellschaft, Leverkusen, Germany

[21] Appl. No.: 230,187

[22] Filed: Apr. 20, 1994

[30] Foreign Application Priority Data

Apr. 27, 1993 [DE] Germany ............... 43 13 693.1

[51] Int. Cl.$^6$ ............... C07D 401/04; C07D 401/14; A61K 31/47; A61K 31/44
[52] U.S. Cl. ............... 514/314; 546/167; 546/116
[58] Field of Search ............... 546/167, 116; 514/314

[56] References Cited

U.S. PATENT DOCUMENTS

| | | | |
|---|---|---|---|
| 3,862,162 | 1/1975 | Meyer et al. | 546/310 |
| 3,989,708 | 11/1976 | Meyer et al. | 546/310 |
| 4,532,248 | 7/1985 | Franckowiak et al. | 514/302 |
| 5,100,900 | 3/1992 | Stoltefuss | 514/314 |
| 5,204,472 | 4/1993 | Stoltefuss | 546/168 |
| 5,225,558 | 7/1993 | Stoltefuss | 546/167 |

FOREIGN PATENT DOCUMENTS 0073997  3/1983  European Pat. Off. .

*Primary Examiner*—C. Warren Ivy
*Assistant Examiner*—D. Margaret M. Mach
*Attorney, Agent, or Firm*—Sprung Horn Kramer & Woods

[57] ABSTRACT

The present invention relates to new 2-amino-4-quinolyl-1,4-dihydropyridines of the general formula (I)

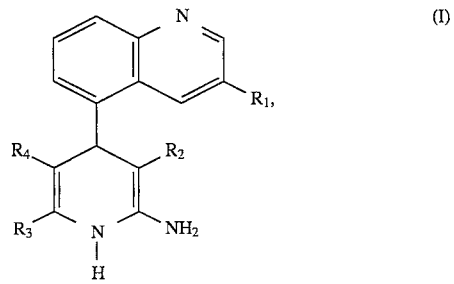

in which $R_1$–$R_4$ have the meaning given in the description, to processes for their preparation and to their use in medicaments, especially in agents for the treatment of cardiac circulatory disorders.

6 Claims, No Drawings

2-AMINO-4-QUINOLYL-DIHYDROPYRIDINES, PROCESSES FOR THEIR PREPARATION, AND THEIR USE

The present invention relates to new 2-amino-4-quinolyl-1,4-dihydropyridines, to processes for their preparation and to their use in medicaments, especially in agents for the treatment of cardiac circulatory disorders.

It is already known that some 2- and 6-amino-3,4-dihydropyridines possess an antiarrhythmic action and also act to inhibit lipid absorption [cf. EP 73 997]. 2-amino-1,4-dihydropyridines having a vasodilatory and antihypertensive action have also already been described. Moreover, some of the compounds of the formula (I) according to the invention are covered by the generally very broad definitions in EP 71 819, although this reference does not name any corresponding specific substances.

The present invention relates to 2-amino-4-quinolyl-1,4-dihydropyridines of the general formula (I)

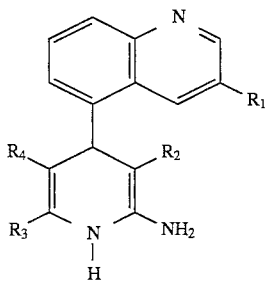

in which $R^1$ represents aryl having from 6 to 10 carbon atoms which is optionally substituted up to 3 times by identical or different substituents comprising halogen, nitro, cyano, trifluoromethyl, trifluoromethoxy, trifluoromethylthio, straight-chain or branched alkoxy or alkoxycarbonyl having in each case up to 8 carbon atoms, carboxyl, amino, dimethylamino or hydroxyl, or by straight-chain or branched alkyl having up to 8 carbon atoms, which may in turn be substituted by aryl having from 6 to 10 carbon atoms, or represents thienyl or pyridyl which are optionally substituted by halogen, $R^2$ represents a group of the formula $-CO-NR^5R^6$ or $-CO-A-R^7$, in which $R^5$ and $R^6$ are identical or different and denote hydrogen, a straight-chain, branched, cyclic, saturated or unsaturated hydrocarbon radical having up to 8 carbon atoms which is optionally substituted by halogen, hydroxyl or cyano or by aryl, aryloxy or arylthio having in each case from 6 to 10 carbon atoms or by a 5- to 7-membered, saturated or unsaturated heterocycle having up to 3 heteroatoms from the series S, N or O, where the carbocycles and heterocycles may in turn be substituted by halogen or cyano or by straight-chain or branched alkyl, alkoxy, alkylthio, alkoxycarbonyl, halogenoalkyl, halogenoalkoxy or halogenoalkylthio having in each case up to 4 carbon atoms, or denote aryl having from 6 to 10 carbon atoms or a 5- to 7-membered, saturated or unsaturated heterocycle having up to 3 heteroatoms from the series S, N or O, which are optionally substituted up to 2 times by identical or different substituents comprising halogen or cyano or by straight-chain or branched alkyl, alkoxy, alkylthio, alkoxycarbonyl, halogenoalkyl, halogenoalkoxy or halogenoalkylthio having in each case up to 4 carbon atoms, or $R^5$ and $R^6$, together and including the nitrogen atom, form a 3- to 8-membered, saturated or unsaturated heterocycle which may optionally be interrupted by an oxygen atom or by a radical of the formula $S(O)_a$, $-CO-$ or $-NR^8$, in which a denotes a number 0, 1, or 2, $R^8$ denotes hydrogen or aryl having from 6 to 10 carbon atoms which is optionally substituted up to 2 times by identical or different substituents comprising halogen or cyano or by straight-chain or branched alkyl, alkoxy, alkylthio, alkoxycarbonyl, halogenoalkyl, halogenoalkoxy or halogenoalkylthio having in each case up to 4 carbon atoms, or denotes a cyclic, saturated or unsaturated, straight-chain or branched hydrocarbon radical having up to 8 carbon atoms which is optionally substituted by hydroxyl or halogen or by aryl having from 6 to 10 carbon atoms or a 5- to 7-membered, saturated or unsaturated heterocycle having 3 heteroatoms from the series S, N or O, which may in turn be substituted up to 2 times by identical or different substituents comprising halogen or cyano or by straight-chain or branched alkyl, alkoxy, alkylthio, alkoxycarbonyl, halogenoalkyl, halogenoalkoxy or halogenoalkylthio having in each case up to 4 carbon atoms, and the heterocycle is optionally substituted by straight-chain or branched alkoxy or alkylthio having in each case up to 4 carbon atoms, halogen, aryl having from 6 to 10 carbon atoms, a 5- to 7- membered, saturated or unsaturated heterocycle having up to 3 heteroatoms from the series S, N or O or by straight-chain or branched alkyl having up to 4 carbon atoms which is optionally substituted in turn by aryl having from 6 to 10 carbon atoms, A denotes a direct bond or an oxygen atom, $R^7$ denotes hydrogen or aryl having from 6 to 10 carbon atoms or a 5- to 7-membered, saturated or unsaturated heterocycle having up to 3 heteroatoms from the series S, N or O, which are optionally substituted up to 3 times by identical or different substituents comprising halogen or cyano or by straight-chain or branched alkyl, alkoxy, alkylthio, alkoxycarbonyl, halogenoalkyl, halogenoalkoxy or halogenoalkylthio having in each case up to 4 carbon atoms, or denotes a cyclic, straight-chain or branched, saturated or unsaturated hydrocarbon radical having up to 10 carbon atoms which is optionally interrupted up to 3 times by identical or different interruptions comprising oxygen or $-CO-$, $-CO-NH-$, $-O-CO-$, $-CO-O-$, $-NH-CO-$, $-SO_2-NH-$, $-NH-SO_2-$, $-S(O)_b-$ or $-NR^9$, in which b has the meaning of a given above, and is identical or different to the latter, $R^9$ has the meaning of $R^8$ given above, and is identical or different to the latter, or the hydrocarbon radical is optionally interrupted up to 3 times by identical or different interruptions comprising arylidene having from 6 to 10 carbon atoms or heterocyclic radicals of the formula

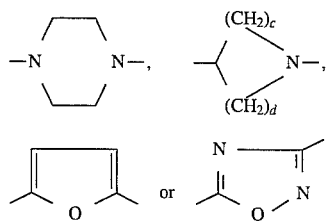

in which c and d are identical or different and denote the number 1 or 2, and in which arylidene may in turn be substituted by halogen or cyano or by straight-chain or branched alkyl, alkoxy, alkylthio, alkoxycarbonyl, halogenoalkyl, halogenoalkoxy or halogenoalkylthio having in each case up to 4 carbon atoms, and where the hydrocarbon radical is optionally substituted up to 3 times by identical or different substituents comprising cycloalkyl having from 3 to 8 carbon atoms, halogen, nitro, cyano, hydroxyl, —O—$NO_2$ or straight-chain or branched alkylthio, alkoxy or acyloxy having in each case up to 8 carbon atoms, or by aryl, aryloxy or arylthio having in each case from 6 to 10 carbon atoms or by a 5- to 7-membered, saturated or unsaturated heterocycle having up to 3 heteroatoms from the series S, N or O, which may in turn be substituted up to 3 times by identical or different substituents comprising halogen or cyano or by straight-chain or branched alkyl, alkoxy, alkylthio, alkoxycarbonyl, halogenoalkyl, halogenoalkoxy or halogenoalkylthio having in each case up to 4 carbon atoms, or is substituted by a group of the formula —$CO_2$—$R^{10}$, —$CONR^{11}R^{12}$ or —$NR^{13}R^{14}$, in which $R^{10}$ has the meaning of $R^8$ given above, and is identical or different to the latter and $R^{11}$, $R^{12}$, $R^{13}$ and $R^{14}$ have the meaning of $R^5$ and $R^6$ given above, and are identical or different to the latter, $R^3$ represents hydrogen or straight-chain or branched alkyl having up to 8 carbon atoms, $R^4$ represents nitro or formyl or $R^3$ and $R^4$ together form a lactone ring of the formula

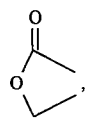

and salts thereof.

Physiologically acceptable salts may be salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids, such as, for example, acetic acid, maleic acid, fumaric acid, malic acid, citric acid, tartaric acid, lactic acid or benzoic acid, or methanesulphonic acid, ethanesulphonic acid, phenylsulphonic acid, toluenesulphonic acid or naphthalenedisulphonic acid.

The compounds according to the invention exist in stereoisomeric forms which are either mirror images of one another (enantiomers) or otherwise (diastereomers). The invention relates both to the isomers and to the racemic forms, as well as to the mixtures of diastereomers. Both the racemic forms and the diastereomers can be separated in a known manner into the stereoisomerically uniform constituents.

Preferred compounds of the general formula (I) are those in which $R^1$ represents phenyl which is optionally substituted up to 2 times by identical or different substituents comprising halogen, nitro, cyano or trifluoromethyl or by straight-chain or branched alkyl or alkoxy having in each case up to 6 carbon atoms, carboxyl, amino, dimethylamino or hydroxyl, or represents thienyl or pyridyl which are optionally substituted by fluorine, chlorine or bromine, $R^2$ represents a group of the formula —CO—$NR^5R^6$ or —CO—A—$R^7$, in which $R^5$ and $R^6$ are identical or different and denote hydrogen or a straight-chain, branched, cyclic, saturated or unsaturated hydrocarbon radical having up to 6 carbon atoms which is optionally substituted by fluorine or chlorine or by phenyl which may in turn be substituted by fluorine or chlorine or by straight-chain or branched alkyl, alkoxy or alkylthio having in each case up to 4 carbon atoms, trifluoromethyl or trifluoromethoxy, or denote phenyl which is optionally substituted by fluorine, chlorine, bromine or cyano or by straight-chain or branched alkyl, alkoxy, alkylthio, or alkoxycarbonyl having in each case up to 4 carbon atoms, trifluoromethyl or trifluoromethoxy, or $R^5$ and $R^6$, together and including the nitrogen atom, form a 5- to 6-membered, saturated or unsaturated heterocycle which may optionally be interrupted by a radical of the formula —$NR^8$, in which $R^8$ denotes hydrogen or phenyl which is optionally substituted by fluorine, chlorine, bromine or cyano or by straight-chain or branched alkyl, alkoxy, alkylthio or alkoxycarbonyl having in each case up to 3 carbon atoms, trifluoromethyl or trifluoromethoxy, or denotes a cyclic, saturated or unsaturated, straight-chain or branched hydrocarbon radical having up to 6 carbon atoms which is optionally substituted by hydroxyl, fluorine, chlorine or bromine or by phenyl or pyridyl which may in turn be substituted up to 2 times by identical or different substituents comprising fluorine, chlorine, bromine or cyano or by straight-chain or branched alkyl, alkoxy, alkylthio or alkoxycarbonyl having in each case up to 4 carbon atoms, trifluoromethyl or trifluoromethoxy, A denotes a direct bond or an oxygen atom, $R^7$ denotes hydrogen or phenyl or pyridyl which are optionally substituted by fluorine or chlorine or by straight-chain or branched alkyl, alkoxy or alkylthio having in each case up to 4 carbon atoms, trifluoromethyl or trifluoromethoxy, or denotes a cyclic, straight-chain or branched, saturated or unsaturated hydrocarbon radical having up to 8 carbon atoms which is optionally interrupted up to 2 times by identical or different interruptions comprising oxygen or —CO—, —CO—NH—, —O—CO—, —CO—O—, —NH—CO—, —$SO_2$—NH—, —NH—$SO_2$, —$S(O)_b$— or —$NR^9$, in which b denotes a number 0, 1 or 2, $R^9$ has the meaning of $R^8$ given above, and is identical or different to the latter, or the hydrocarbon radical is optionally interrupted up to 2 times by identical or different interruptions comprising phenylidene or heterocyclic radicals of the formula

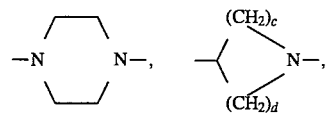

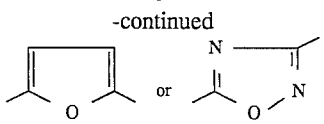

in which c and d are identical or different and denote the number 1 or 2, and where the hydrocarbon radical is optionally substituted up to 2 times by identical or different substituents comprising cyclopropyl, cyclobutyl, cyclopentyl, cyclohexyl, fluorine, chlorine, bromine, nitro, cyano, hydroxyl, —O—NO$_2$ or straight-chain or branched alkylthio, alkoxy or acyloxy having in each case up to 6 carbon atoms, or by phenyl, phenoxy or phenylthio or pyridyl which may in turn be substituted by fluorine or chlorine or by straight-chain or branched alkyl, alkoxy, alkylthio or alkoxycarbonyl having in each case up to 4 carbon atoms, trifluoromethyl or trifluoromethoxy, or is substituted by a group of the formula —CO$_2$—R$^{10}$, —CONR$^{11}$R$^{12}$ or —NR$^{13}$R$^{14}$, in which $R^{10}$ has the meaning of $R^8$ given above, and is identical or different to the latter and $R^{11}$, $R^{12}$, $R^{13}$ and $R^{14}$ have the meaning of $R^5$ and $R^6$ given above, and are identical or different to the latter, $R^3$ represents hydrogen or straight-chain or branched alkyl having up to 4 carbon atoms, $R^4$ represents nitro or formyl or $R^3$ and $R^4$ together form a lactone ring of the formula

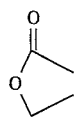

and salts thereof.

Particularly preferred compounds of the general formula (I) are those
in which $R^1$ represents phenyl which is optionally substituted up to 2 times by identical or different substituents comprising fluorine, chlorine, nitro, trifluoromethyl, methyl, ethyl, methoxy, ethoxy, dimethylamino or hydroxyl, or represents thienyl or pyridyl, $R^2$ represents a group of the formula —CO—NR$^5$R$^6$ or —CO—A—R$^7$, in which $R^5$ and $R^6$ are identical or different and denote hydrogen or a straight-chain, branched, cyclic, saturated or unsaturated hydrocarbon radical having up to 5 carbon atoms which is optionally substituted by fluorine or chlorine or by phenyl which may in turn be substituted by fluorine, chlorine, methyl, methoxy, methylthio, trifluoromethyl or trifluoromethoxy, or denote phenyl which is optionally substituted by fluorine or chlorine or by methyl, methoxy, trifluoromethyl or trifluoromethoxy, or $R^5$ and $R^6$, together and including the nitrogen atom, form a 5- to 7-membered, saturated or unsaturated heterocycle which may optionally be interrupted by an oxygen atom or by a radical of the formula —NR$^8$, in which $R^8$ denotes hydrogen or phenyl, or denotes a cyclic, saturated or unsaturated, straight-chain or branched hydrocarbon radical having up to 4 carbon atoms which is optionally substituted by fluorine, chlorine or bromine or by phenyl, A denotes a direct bond or an oxygen atom, $R^7$ denotes hydrogen or phenyl, or denotes a cyclic, straight-chain or branched, saturated or unsaturated hydrocarbon radical having up to 8 carbon atoms which is optionally interrupted by oxygen or by —CO—, —CO—NH—, —O—CO—, —CO—O—, —NH—CO—, —SO$_2$—NH—, —NH—SO$_2$, —S(O)$_b$— or —NR$^9$, in which b denotes a number 0, 1 or 2, $R^9$ has the meaning of $R^8$ given above, and is identical or different to the latter, or the hydrocarbon radical is interrupted up to 2 times by identical or different interruptions comprising phenylidene or heterocyclic radicals of the formula

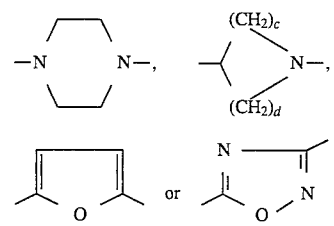

in which c and d are identical or different and denote a number 1 or 2, and where the hydrocarbon radical is optionally substituted up to 2 times by identical or different substituents comprising cyclopropyl, cyclobutyl, cyclopentyl, cyclohexyl, fluorine, chlorine, nitro, cyano, hydroxyl, —O—NO$_2$ or straight-chain or branched alkylthio, alkoxy or acyloxy having in each case up to 4 carbon atoms, or by phenyl, phenoxy, phenylthio or pyridyl which may in turn be substituted by fluorine or chlorine or by alkyl, alkoxy, alkylthio or alkoxycarbonyl having in each case up to 2 carbon atoms, trifluoromethyl or trifluoromethoxy, or is substituted by a group of the formula —CO$_2$—R$^{10}$, —CONR$^{11}$R$^{12}$ or —NR$^{13}$R$^{14}$, in which $R_{10}$ has the meaning of $R^8$ given above, and is identical or different to the latter and $R^{11}$, $R^{12}$, $R^{13}$ and $R^{14}$ have the meaning of $R^5$ and $R^6$ given above, and are identical or different to the latter, $R^3$ represents hydrogen, methyl or ethyl, $R^4$ represents nitro or formyl, or $R^3$ and $R^4$ together form a lactone ring of the formula

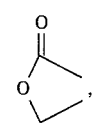

and salts thereof.

Very particularly preferred compounds of the general formula (I) are those
in which $R^1$ represents phenyl which is optionally substituted by fluorine, chlorine, methyl or methoxy, $R^2$ represents a group of the formula —CO—A—$R^7$, in which A denotes an oxygen atom, $R^7$ denotes hydrogen or a cyclic, straight-chain or branched, saturated or unsaturated hydrocarbon radical having up to 8 carbon atoms which is optionally interrupted by oxygen, sulphur, $SO_2$, —CO—NH—, —NH—CO— or —CO—O and which is optionally substituted by cyclopropyl, cyclopentyl, cyclohexyl, fluorine or chlorine or by phenyl, phenoxy or phenylthio, where the rings may in turn be substituted by fluorine, chlorine, methyl or methoxy, $R^3$ represents hydrogen or methyl, $R^4$ represents nitro, or $R^3$ and $R^4$ together form a lactone ring of the formula

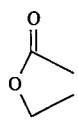

and salts thereof.

The preparation of the compounds of the general formula (I) according to the invention is characterized in that

[A] either aldehydes of the general formula (II)

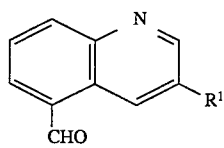

in which $R^1$ has the meaning given above, are reacted directly with compounds of the general formula (III)

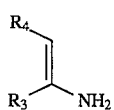

in which $R^3$ and $R^4$ have the meaning given above, and compounds of the tautomeric formulae (IV) and (IVa)

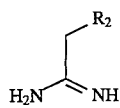

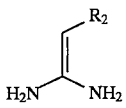

in which $R^2$ has the meaning given above, in inert solvents at temperatures of between 10° C. and 150° C., or

[B] Compounds of the general formula (II) are reacted with compounds of the general formula (V)

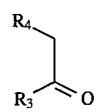

in which $R^3$ and $R^4$ have the meaning given above and, after optionally isolating the ylidene compounds of the general formula (VI)

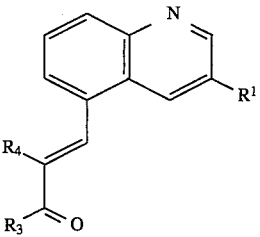

in which $R^1$, $R^3$ and $R^4$ have the meaning given above, they are reacted with compounds of the general formula (VII) or (VIIa)

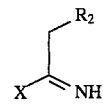

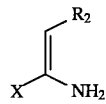

in which $R^2$ has the meaning given above and

X represents the amino group or $C_1$–$C_4$-alkoxy, optionally in the presence of inert organic solvents at temperatures of from 10° C. to 150° C.; where, in the case where X represents $C_1$–$C_4$-alkoxy, ammonium salts such as ammonium acetate are added, or, in the case where $R^3$ and $R^4$ together form a lactone ring,

[C] initially, by the methods given in [A] and [B], compounds of the general formula (VIII)

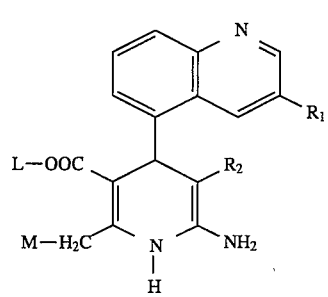

are prepared in which $R_1$, $R^2$ and $R^3$ have the meaning given above,

L represents a $C_1$–$C_8$-alkyl radical and

M represents a leaving group such as, for example, chlorine or acetoxy, followed by an acid- or base-catalysed cyclization by known methods.

In the case of the pure enantiomers, either the resultant mixture of diastereomers of the respective compounds of the general formula (I) in which $R^2$ represents a defined chiral radical is first separated, then converted to the corresponding carboxylic acids ($R^2=CO_2H$) which, in a final step, are esterified, or the respective diastereomers are transesterified directly using the corresponding alcohols, in particular in the form of the alcoholates.

The processes according to the invention can be illustrated by way of example using the following formula scheme:

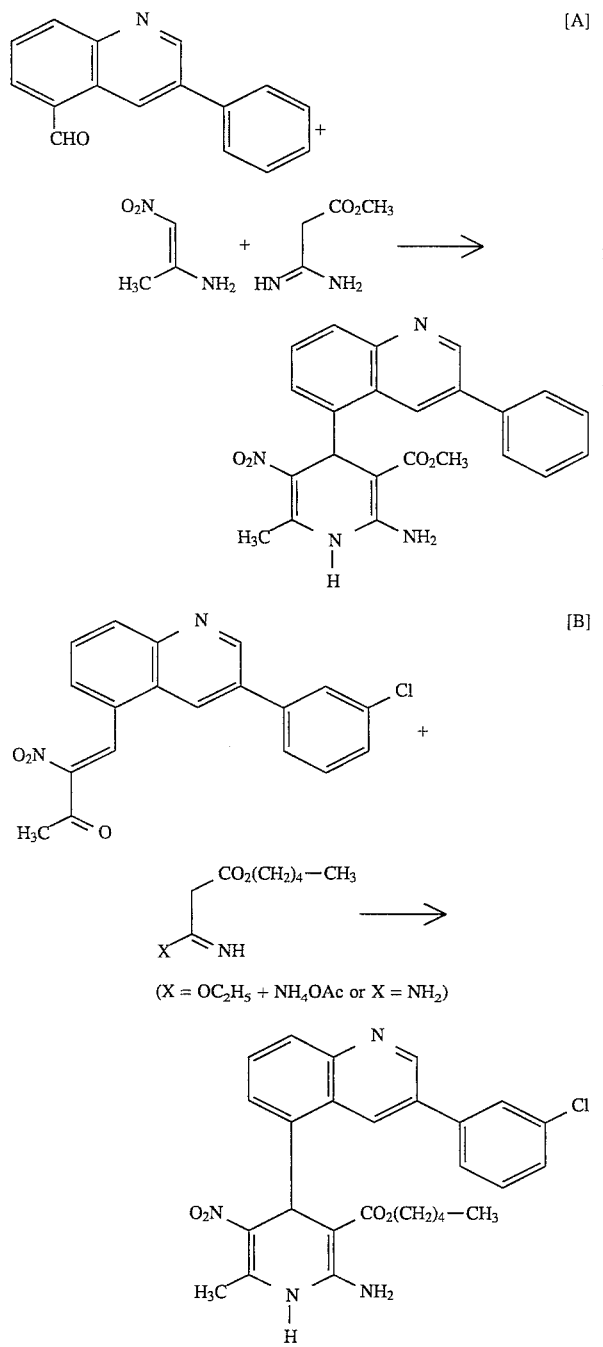

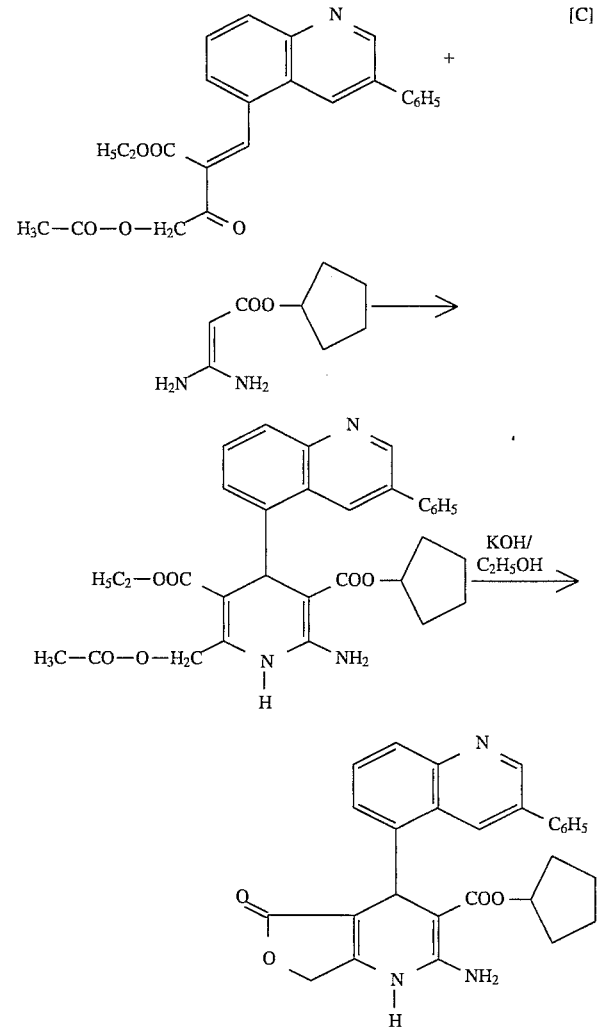

Suitable solvents in this context are all inert organic solvents which are not altered under the reaction conditions. Preferred such solvents include alcohols such as methanol, ethanol, propanol or isopropanol, or ethers such as diethyl ether, dioxane, tetrahydrofuran, glycol dimethyl ether or diethylene glycol dimethyl ether, acetonitrile, or amides such as hexamethylphosphoric triamide or dimethylformamide, or acetic acid or halogenated hydrocarbons such as methylene chloride, carbon tetrachloride or hydrocarbons such as benzene or toluene. It is also possible to use mixtures of the solvents mentioned. Preferred solvents, depending on the particular process variant [A], [B] or [C], are methanol, isopropanol, ethanol and n-propanol, acetonitrile or tetrahydrofuran.

The reaction temperatures can be varied within a relatively wide range. The reaction is in general carried out at between +10° C. and +150° C., preferably between +20° C. and 100° C., and, in particular, at the boiling temperature of the respective solvent.

The reaction can be carried out under atmospheric pressure but also under increased or reduced pressure (e.g. 0.5 to 3 bar). It is generally carried out at atmospheric pressure.

Suitable chiral ester radicals are all esters of enantiomerically pure alcohols such as, for example, 2-butanol, 1-phenylethanol, lactic acid, lactic acid esters, mandelic acid, mandelic acid esters, 2-aminoalcohols, sugar derivatives, hydroxyamino acid derivatives and many other enantiomerically pure alcohols.

The separation of the diastereomers is generally carried out either by fractional crystallization, by column chromatography or by Craig partition. Which method is the optimum one must be decided from case to case; sometimes it is also expedient to use combinations of the individual methods. A particularly suitable separation is by crystallization or Craig partition, or by a combination of the two methods.

The compounds of the general formula (II) are in some cases known, and can be prepared by conventional methods by, for example, oxidizing the corresponding alkyl- or hydroxyalkyl-quinolines or reducing the corresponding carboxyquinolines.

As an alternative, it is also possible to react 4-amino-3-hydroxyphthalide, which is obtained by conventional hydrogenation of 4-nitro-3-hydroxyphthalide—known from the literature—in the presence of a catalyst, preferably using palladium/barium sulphate, with compounds of the general formula $R^1$—$CH_2$—CHO, some of which are known, to give compounds of the general formula (II), reaction proceeding via the corresponding carboxylic acids.

The compounds of the general formulae (III), (IV) (IVa), (V), (VI), (VII) and (VIIa) are known or can be prepared by methods known from the literature.

The compounds of the general formula (VIII) are new, but can likewise be prepared by known methods.

The compounds of the formula (I) according to the invention exhibit an unforeseeable and valuable spectrum of pharmacological action. They influence myocardial contractility and smooth-muscle tone. They preferably have a positively inotropic action. They can therefore be employed in pharmaceuticals for influencing pathologically altered blood pressure, in coronary therapy, and for treating cardiac insufficiency. They can also be used for treating cardiac arrhythmias, for reducing the level of blood sugar, for decongesting the mucosae and for influencing the salt and fluid balance.

The cardiac and vascular actions were demonstrated on the guinea-pig heart perfused in isolation. For this purpose, the hearts of guinea pigs weighing from 250 to 350 g are used. The animals are sacrificed by a blow to the head, the thorax is opened, and a metal cannula is inserted and attached in the exposed aorta. The heart and the lungs are excised from the thorax and connected via an aortic cannula, to the perfusion apparatus in the course of perfusion. The lungs are separated at the roots. The perfusion medium used is a Krebs-Henseleit solution (118.5 mmol/l of NaCl, 4.75 mmol/l of KCl, 1.19 mmol/l of $KH_2PO_4$, 1.19 mmol/l of $MgSO_4$, 25 mmol/l of $NaHCO_3$ and 0.013 mmol/l of $Na_2EDTA$) with a $CaCl_2$ content of 1.2 mmol/l. The energy-supplying substrate added is glucose at 10 mmol/l. Prior to the perfusion, the solution is filtered to remove all particles. The solution is gassed with carbogen (95% $O_2$, 5% $CO_2$,) to maintain a pH of 7.4. The hearts are perfused at 32° C. at a constant flow rate (10 ml/min) using a peristaltic pump.

For measuring the cardiac function, a liquid-filled latex balloon which is connected via a liquid column to a pressure transducer is inserted through the left atrium into the left ventricle, and the isovolumetric contractions are recorded on a rapid recorder. The perfusion pressure is recorded using a pressure transducer which is connected to the perfusion system upstream of the heart. Under these conditions, a reduction in the perfusion pressure indicates a coronary dilatation, and an increase or decrease in the amplitude of contraction in the left ventricle indicates a fall or rise, respectively, in myocardial contractility. The compounds according to the invention, in suitable dilutions, are introduced into the perfusion system a short distance upstream of the isolated heart.

The new active compounds can be converted by known methods into the conventional formulations such as coated and uncoated tablets, pills, granules, aerosols, syrups, emulsions, suspensions and solutions, using inert, non-toxic, pharmaceutically appropriate excipients or solvents. In this context, the therapeutically active compound should in each case be present in a concentration of from approximately 0.5 to 90% by weight of the total mixture, i.e. in amounts sufficient to achieve the stated scope of dosage.

The formulations are prepared by, for example, extending the active compounds using solvents and/or excipients, with the optional use of emulsifiers and/or dispersants; where water is used as a diluent, organic solvents may optionally be used as auxiliary solvents.

Administration is effected in a conventional manner, preferably orally or parenterally and, in particular, perlingually or intravenously.

It has in general proved advantageous, in the case of intravenous administration, to administer amounts of from approximately 0.001 to 1 mg/kg, preferably from approximately 0.01 to 0.5 mg/kg of body weight in order to achieve effective results; in the case of oral administration, the dosage is from approximately 0.01 to 20 mg/kg, preferably from 0.1 to 10 mg/kg of body weight.

Despite this, it may be necessary to depart from the stated amounts, specifically in dependence on the body weight or on the nature of the administration route, on the individual response to the medicament, on the nature of its formulation and on the time at or over which administration is effected. For instance, it may in some cases be sufficient to use less than the minimum amount stated above, while in other cases the upper limit mentioned has to be exceeded. In the case where greater quantities are administered, it may be advisable to divide these into two or more individual doses over the day.

EXAMPLE 1

Ethyl 2-amino-6-methyl-5-nitro-4- (3-phenyl-5-quinolyl)-1, 4-dihydropyridine-3- carboxylate

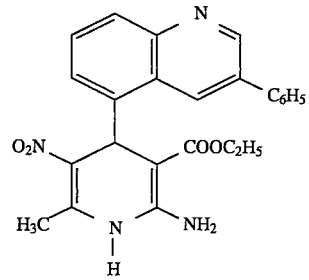

1.66 g (10 mmol) of ethyl amidinoacetate hydrochloride, 1.8 g (17.5 mmol) of nitroacetone and 820 mg (10 mmol) of sodium acetate are added to 2.33 g (10 mmol) of 3-phenylquinoline-5-carbaldehyde in 20 ml of ethanol, and the mixture is heated at reflux for 30 min. The dark red solution obtained is cooled and concentrated. The residue is dissolved in ethyl acetate/water, the phases are separated, and the ethyl acetate phase is extracted with sodium hydrogen carbonate solution and water, dried and concentrated. The mixture obtained is purified on a silica gel column using toluene/ethyl acetate in a volume ratio of 2:1. The pure fractions are collected and concentrated. By crystallization from acetonitrile, 116 mg of yellow crystals with a melting point of 252°–253° C. are obtained.

EXAMPLE 2

Isopropyl 2-amino-4-(3-phenyl-5-quinolyl)-5-oxo-1,4,5,7-tetrahydrofuro[3,4-b]pyridine-3-carboxylate

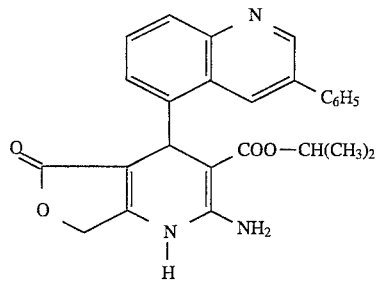

1.2 g (3 mmol) of ethyl 2-(3-phenyl-5-quinolylydene)4-acetoxy-3-oxo-butyrate in 15 ml of isopropanol are heated at reflux overnight with 0.54 g (3 mmol) of isopropyl amidinoacetate hydrochloride and 0.25 g (3 mmol) of sodium acetate. The mixture is cooled and concentrated. The residue obtained is triturated with water and filtered off with suction.

0.25 g of potassium hydroxide is added to 0.53 g of the intermediate compound in 15 ml of methanol, and the mixture is heated at reflux for 1 hour. It is cooled and neutralized with 4.5 ml of 1N hydrochloric acid. The crystals which have precipitated are filtered off with suction and washed with methanol. 290 mg of colourless crystals with a melting point of 199° C. are obtained.

The compounds listed in Tables 1 and 2 are prepared in analogy to the procedures of Examples 1 and 2:

TABLE 1

| Ex. No. | $R^2$ | Z | m.p. °C. |
|---|---|---|---|
| 3 | $-CO_2-(CH_2)_2-CH_3$ | H | 187 |
| 4 | $-CO_2-CH_3$ | H | 220 |
| 5 | $-CO_2-CH(CH_3)_2$ | p-F | 205 |
| 6 | $-CO_2C_2H_5$ | p-F | 204 |
| 7 | $-CO_2-(CH_2)_2OCH_3$ | H | 172 |
| 8 | $-CO_2-C_2H_5$ | H | 273 |
| 9 | $-CO_2-(CH_2)_2-OC_2H_5$ | H | 157 |
| 10 | $-CO_2-CH(CH_3)_2$ | H | 199 |
| 11 | $-CO_2CH_3$ | m-$CH_3$ | 203 |
| 12 | $-CO_2(CH_2)_2-OCH_3$ | p-Cl | 160–162 |
| 13 | $-CO_2CH(CH_3)_2$ | p-Cl | 195–197 |
| 14 | $-CO_2CH_3$ | m-$OCH_3$ | 185 |
| 15 | $-CO_2-CH(CH_3)_2$ | m-$OCH_3$ | 168 |
| 16 | $-CO_2CH_3$ | p-Cl | 241–242 |
| 17 | $-CO_2C_2H_5$ | H | 185 |

TABLE 2

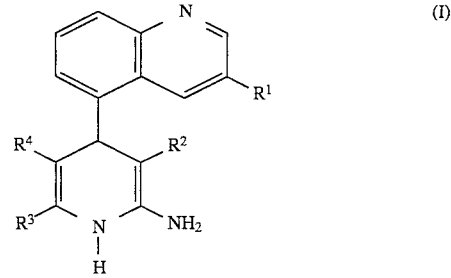

| Ex. No. | $R^2$ | Z | m.p. °C. |
|---|---|---|---|
| 18 | $-CO_2-(CH_2)_2-CH_3$ | H | 229–231 |
| 19 | $-CO_2-(CH_2)_2-OCH_3$ | H | 247 |
| 20 | $-CO_2-CH(CH_3)_2$ | H | 245–246 |

We claim:
1. A 2-amino-4-quinolyl-1,4-dihydropyridine of the formula

$$\text{(I)}$$

in which $R^1$ represents phenyl which is optionally substituted up to 2 times by identical or different substituents selected from the group consisting of fluorine, chlorine, nitro, trifluoromethyl, methyl, ethyl, methoxy, ethoxy, dimethylamino or hydroxyl, or represents thienyl or pyridyl, $R^2$ represents a group of the formula $-CO-NR^5R^6$ or $-CO-A-R^7$, in which $R^5$ and $R^6$ are identical or different and denote hydrogen or a straight-chain, branched, cyclic, saturated or unsaturated hydrocarbon radical having up to 5 carbon atoms which is optionally substituted by, fluorine or chlorine or by phenyl which is optionally substituted by fluorine chlorine, methyl, methoxy, methylthio, trifluoromethyl or trifluoromethoxy, or denote phenyl which is optionally substituted by fluorine or chlorine or by methyl, methoxy, trifluoromethyl or trifluoromethoxy, A denotes a direct bond or an oxygen atom, $R^7$ denotes hydrogen or phenyl, or denotes a, straight-chain or branched, saturated or unsaturated hydrocarbon radical having up to 8 carbon atoms which is optionally interrupted by oxygen or by $-CO-$, $-CO-NH-$, $-O-CO-$, $-CO-O-$, $-NH-CO-$, $-SO_2-NH-$, $-NH-SO_2-$, $-S(O)_b-$ or $-NR^9$, in which b denotes a number 0, 1 or 2, $R^9$ denotes hydrogen or phenyl, or denotes a cyclic, saturated or unsaturated, straight-chain or branched hydrocarbon radical having up to 4 carbon atoms which is optionally substituted by fluorine, chlorine or bromine or by phenyl, or the hydrocarbon radical is interrupted up to 2 times by identical or different interruptions selected from the group consisting of phenylidene, and where the hydrocarbon radical is optionally substituted up to 2 times by identical or different substituents wherein said substituents are cyclopropyl, cyclobutyl, cyclopentyl, cyclohexyl, fluorine, chlorine, nitro, cyano, hydroxyl, —O—$NO_2$ or straight-chain or branched alkylthio, alkoxy or acyloxy having in each case up to 2 carbon atoms, trifluoromethyl or trifluoromethoxy, or is substituted by a group of the formula —$CO_2$—$R^{10}$, —$CONR^{11}R^{12}$ or —$NR^{13}R^{14}$, in which $R^{10}$ has the meaning of $R_9$ given above, and is identical or different to the latter, and $R^{11}$, $R^{12}$, $R^{13}$ and $R^{14}$ have the meaning of $R^5$ and $R^6$ given above, and are identical or different to the latter, $R^3$ represents hydrogen, methyl or ethyl, $R^4$ represents nitro or formyl, or $R^3$ and $R^4$ together form a lactone ring of the formula

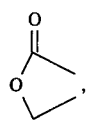

or salt thereof.

2. A 2-amino-4-quinolyl-1,4-dihydropyridine according to claim 1, in which $R^1$ represents phenyl which is optionally substituted by fluorine, chlorine, methyl or methoxy, $R^2$ represents a group of the formula —COA—$R^7$, in which A denotes an oxygen atom, $R^7$ denotes hydrogen or a straight-chain or branched, saturated or unsaturated hydrocarbon radical having up to 8 carbon atoms which is optionally interrupted by oxygen, sulphur, $SO_2$, —CO—NH—, —NH—CO— or —CO—O and which is optionally substituted by cyclopropyl, cyclopentyl, cyclohexyl, fluorine or chlorine or by phenyl, phenoxy or phenylthio, where the rings are optionally substituted by fluorine, chlorine, methyl or methoxy, $R^3$ represents hydrogen or methyl, $R^4$ represents nitro, or $R^3$ and $R^4$ together form a lactone ring of the formula

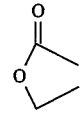

or a salt thereof.

3. A method of treatment of cardiac disorders by influencing myocardial contractility and smooth muscle tone which comprises administering an effective amount of at least one compound according to claim 1 to a host in need thereof.

4. A compound of the formula

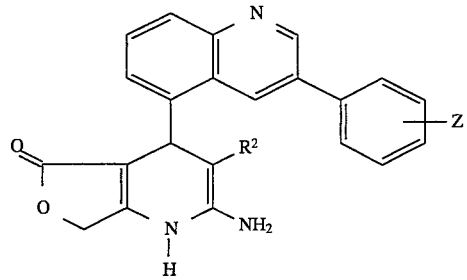

in which $R_2$ represents the group $CO_2(CH_2)_2$—$CH_3$ and

Z represents hydrogen, halogen or methoxy.

5. A compound according to claim 1 wherein $R^4$ is formyl.

6. A composition comprising an effective amount of at least one compound according to claim 1 and an inert carrier.

* * * * *

UNITED STATES PATENT AND TRADEMARK OFFICE
CERTIFICATE OF CORRECTION

PATENT NO. : 5,502,062
DATED : March 26, 1996
INVENTOR(S) : Stoltefuss, et al.

It is certified that error appears in the above-indentified patent and that said Letters Patent is hereby corrected as shown below:

Col. 15, line 13    Delete " $R_9$ " and substitute -- $R^9$ --

Signed and Sealed this

Sixth Day of August, 1996

*Attest:*

BRUCE LEHMAN

*Attesting Officer*     *Commissioner of Patents and Trademarks*